United States Patent [19]

Fraser

[11] Patent Number: 5,117,691

[45] Date of Patent: Jun. 2, 1992

[54] HEATED ELEMENT VELOCIMETER

[75] Inventor: Allan B. Fraser, Woodbine, Md.

[73] Assignee: The John Hopkins University, Baltimore, Md.

[21] Appl. No.: 491,884

[22] Filed: Mar. 12, 1990

[51] Int. Cl.⁵ .............................................. G01F 1/68
[52] U.S. Cl. ................................ 73/204.15; 73/204.17
[58] Field of Search ............ 73/204.14, 204.15, 204.17, 73/204.25; 374/45

[56] References Cited

U.S. PATENT DOCUMENTS

| | | | |
|---|---|---|---|
| 3,719,083 | 3/1973 | Morris et al. | 73/204.17 X |
| 4,043,196 | 8/1977 | Trageser | 73/204.15 X |
| 4,059,482 | 11/1977 | Bowman | 73/204.17 X |
| 4,335,605 | 6/1982 | Boyd | 73/204.14 |

Primary Examiner—Herbert Goldstein
Attorney, Agent, or Firm—Robert E. Archibald; Francis A. Cooch

[57] ABSTRACT

The present invention is a heated element sensor for detecting the flow rate of a fluid or other physical characteristics of a fluid. The invention teaches driving the thermo-resistive element along a profile having at least two states and measuring the power and temperature of the sensor at each state. In this way a dissipation coefficient can be determined and fluid flow and other physical characteristics determined without the need for ambient temperature to be determined.

19 Claims, 3 Drawing Sheets

HEATED ELEMENT VELOCIMETER

STATEMENT OF GOVERNMENTAL INTEREST

The Government has rights in this invention pursuant to Contract No N00039-89-C-5301, awarded by the Department of the Navy.

BACKGROUND OF THE INVENTION

1. Field of the Invention

The present invention relates to a heated element sensor for detecting the flow rate of a fluid or other physical characteristics of a fluid. The invention uses a continuous waveform excitation to drive a single thermo-resistive element between two or more states.

2. Description of Prior Art

Heated element velocimeters have been known in the art. However, the techniques used to drive the heated element and to relate its temperature to the velocity or other properties of the fluid are significantly different from those described in the present invention.

U.S. Pat. No. 3,603,147 issued to Frank D. Doorman, uses a balancing bridge to supply power to self-heat a single temperature sensor. An amplifier coupled to the bridge produces a pulse output voltage which has a pulse width equal to the time it takes the temperature sensor to heat from ambient to a temperature that balances the bridge. The width of this pulsed output is determined by both the fluid temperature and its flow rate.

U.S Pat. No. 3,905,203 issued to Calvet et al, teaches a means for supplying a first pulse of electrical energy to a single heated thermo-resistive element followed at a preselected interval by at least a second pulse of electrical energy. The short pulses sample the electrical properties of the heated sensing element under two self-heating conditions. The invention requires either finding or extrapolating the ambient fluid temperature from the unexcited sensor. This temperature must then be used as a parameter in the determination of fluid velocity from the measurements.

U.S. Pat. No. 4,501,145 issued to Boegli et al, covers a Katta thermometer with automatic measurement of the time intervals required for a fixed amount of cooling. A weak current is provided to the sensor in order to assess the times required for the probe to reach the various temperature levels as it is equilibrated. From these times, kinetics of cooling at the probe are deduced and properties of fluid flow are computed.

SUMMARY OF THE INVENTION

The present invention teaches the use of a continuous waveform excitation to produce at least two knowable states in a heated element anemometer. The heated element, such as a thermo-resistive element, is driven along a temperature path, and the power necessary to drive the thermo-resistive element along that path is measured. The invention operates without reference to ambient temperature and can be used to measure the velocity of a fluid as well as other thermally related perimeters, such as pressure, composition, viscosity, thermal conductivity, and fluid density.

The invention uses either the mathematical derivative of King's Law or a first difference of King's Law to calculate velocity from the power necessary to drive the thermo-resistive element along points on a temperature path. If a mathematical difference of King's Law is evaluated at fixed flow velocity and two points along a driven temperature path, the $$\frac{P_1 - P_2}{T_1 - T_2} = A + BV^{\frac{1}{2}} \text{ results,} \quad \text{Equation}$$

where A+B are constants, V is velocity of the fluid, T1 and T2 are two temperatures along the periodic temperature path and P1 and P2 are the applied powers required to drive the thermo-resistive element to temperatures T1 and T2.

For a multiple point, continuous periodic temperature waveform, the limiting case where T1−T2 approaches zero produces the following equation: $dP/dT = A + BV^{\frac{1}{2}}$.

In the case of other thermally related variables (X), there are generally functional rules that relate power dissipation to points along the temperature profile: $dP/dT = f(X)$. For instance, with a heated element in a motionless fluid, the functional relationship between power dissipation and points along the driven temperature profile are given by: $a \cdot (dP/dT) = K$ where "a" is a calibration constant for the device and K is the thermal conductivity of the fluid. The present invention operates independent of knowing the ambient temperature in the bulk of the fluid whether the device measures velocity or other thermally related variables.

In its simplest form the present invention has three basic embodiments. In the first embodiment, the thermo-resistive element (which is exposed to fluid) is driven along a temperature path. The temperature path may have at least two stable, or nearly stable, temperature values, such as provided by a square wave function, or it may be continually driven along a periodic path, such as provided by a sinusoidal function. The power required to drive the thermo-resistive element along the path is measured, and flow velocity is calculated using the above equations.

In the second embodiment, the thermo-resistive element is driven along a power path—that is, the power level used to power the thermo-resistive element is driven along a periodic path. Again, the power path, like the temperature path, may have at least two virtually stable power values, such as produced by a square wave function, or it may be continually driven along a periodic path, such as provided by a sinusoidal waveform. Resistance of the thermo-resistive element is measured as it is driven along the power path and its temperature is calculated. Using the formulas cited above, the flow velocity of the fluid across the thermo-resistive element is then calculated.

In the third embodiment the thermo-resistive element is driven along a known path of electrical excitation. The excitation may be controlled by voltage or current. The electrical path causes at least two states to be reached in the sensing element. At each state the temperature of and the drive power into the thermo-resistive sensor are determined, and the cited formulas are used to determine the flow velocity.

DESCRIPTION OF THE PREFERRED EMBODIMENTS

In its generalized embodiment the invention uses a circuit to drive a thermo-resistive element along a temperature path. The conduction of heat away from the thermo-resistive element establishes a means for characterizing flow velocity of the medium surrounding the thermo-resistive element. The power required to drive the thermo-resistive element at each point along the designated temperature path changes depending on the rate at which heat is conducted away from the thermo-resistive element; the rate of heat flow is related to fluid flow rate of the medium by King's Law, which also involves the unknown ambient temperature.

In the simplest embodiment of this invention, King's Law is evaluated at two different driven temperatures $T_1$ and $T_2$. The resulting Equation to calculate the velocity of the medium (V) is:

$$\frac{\Delta P}{\Delta T} = \frac{P_1 - P_2}{T_1 - T_2} = A + BV^{\frac{1}{2}} \qquad \text{Equation 1}$$

where $P_1$ and $P_2$ are the applied powers required to drive the thermo-resistive element at steady state temperatures $T_1$ and $T_2$. The derivation of Equation 1 from King's Law eliminates the unknown ambient temperature. In the case where the power to drive the thermo-resistive element along a given temperature profile uses a continuous waveform, such as a sinusoidal, the velocity equation can be written as:

$$\frac{dP}{dT} = A + BV^{\frac{1}{2}} \qquad \text{Equation 2}$$

Figure 1:
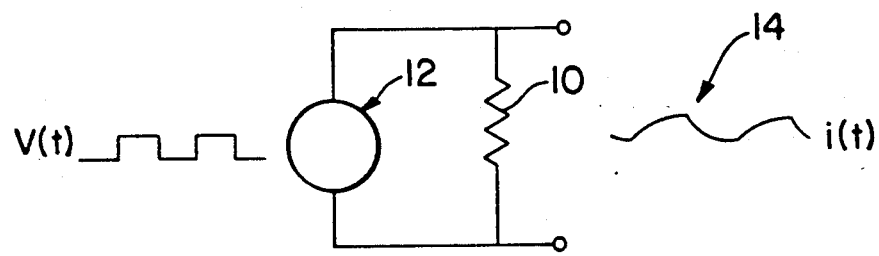
FIG. 1 is a simplified schematic drawing showing an embodiment of the invention wherein an ideal voltage source drives the thermo-resistive element along a periodic path having two stable values of electrical excitation.
Figure 2:
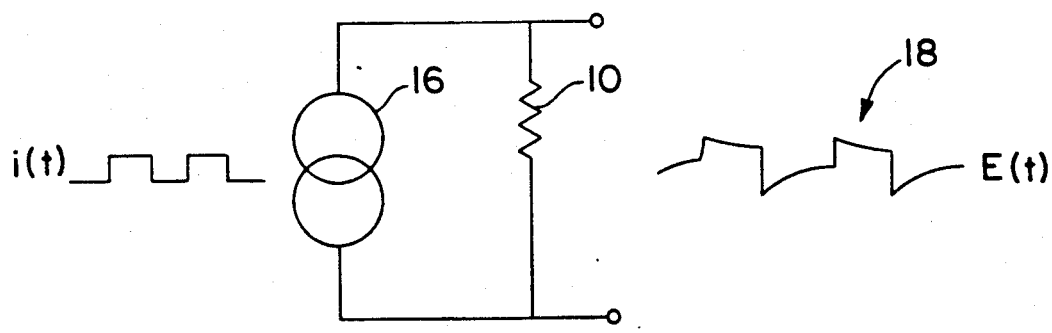
FIG. 2 is a simplified schematic drawing of the invention utilizing an ideal current source to drive the thermo-resistive element along a periodic, path having two stable levels of electrical excitation.

FIGS. 1 and 2 show the simplest forms of the invention. A single sensor, such as a thermo-resistive element is self-heated to measurable temperature states by either switched or continuous waveforms. In the simplest devices, a thermo-resistive element is alternatively driven by two levels of voltage, E, or current, I. These drive devices are "ideal" sources, or virtually so. The corresponding pair of resulting currents or voltages, respectively, are measured after sufficient time has elapsed for virtual equilibration. The thermo-resistive element is thus driven by this circuit to two equilibrium resistances. The resistances are calculated using Ohm's Law, $R = E/I$. The temperature of the thermo-resistive element is calculated from these resistance values since there is a functional relationship particular to each type of thermo-resistive element relating temperature to resistance (i.e., $T = f(R)$). The power at each driven state is calculated from any two of the measured voltage and current values and the calculated resistance (R) using Joule's Law. The temperature (T) and power (P) quantities from the two measurable states are respectively differenced, and the differences are used to form the desired quotient $\Delta T/\Delta P$. In the device in FIG. 1, the thermo-resistive element 10 (for example, a thermistor) is driven by a voltage drive 12 that provides alternating voltage levels. These voltage levels drive the thermo-resistive element (thermistor) 10 between the resulting and to be determined temperatures $T_1$ and $T_2$. The current 14 through the thermistor element is measured and the power dissipation, resistance, and temperature are determined. FIG. 2 shows a similar device except that the thermo-resistive element 10 is driven by a current drive 16. The current drive produces two current levels which drive the thermo-resistive element 10 along a path reaching two final soluble temperature states $T_1$ and $T_2$. The voltage 18 across the thermistor 10 is measured and the power dissipation, resistance, and temperature are calculated. In both cases, Equation 1 is used to calculate the fluid velocity (V) from the power required to drive the thermo-resistive element along the designated temperature profile.

Alternating Gain Temperature Servo Embodiment

Figure 3:
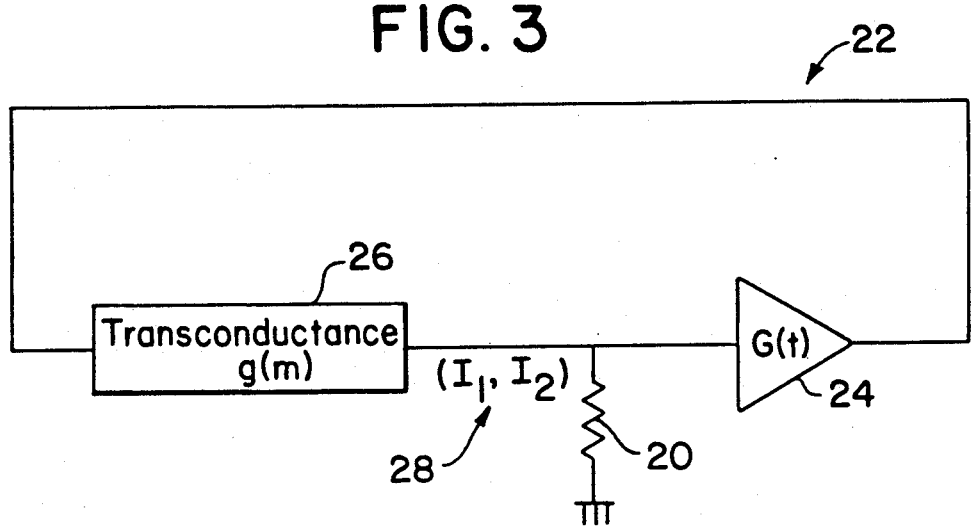
FIG. 3 is a schematic of the invention using a temperature servo to drive the thermo-resistive element to fixed temperature points.

FIG. 3 illustrates an embodiment of the present invention using a temperature servo to drive the thermo-resistive element to fixed temperature end points. In this embodiment, the temperature of the thermo-resistive element 20 is driven along a path and the power variation necessary to drive the thermo-resistive element between the temperature end points along the path is calculated. This calculated power fluctuation is indicative of fluid velocity across the thermo-resistive element according to Equation 2. The feedback loop 22 employs positive electrical feedback but is stable because the resistance of the thermo-resistive element 20 drops as it becomes warmer. (For this particular circuit the thermo-resistive element must have a negative temperature coefficient.) The amplifier 24 produces a gain, G, that varies periodically with time. The transconductance, $g_m$, of the voltage-controlled current source, 26, may be varied in time as easily as the gain, G, of the buffer amplifier, 24. Solution of the circuit equation describing FIG. 3 reveals that the resistance of the thermo-resistor, 20, controlled at equilibrium by $$R = 1/g_m G. \qquad \text{Equation 3}$$

In the simplest embodiment, the amplifier 24 alternatively produces two gains G1, G2. The transconductor 26 acts as a voltage-controlled current source with a transconductance of $g_m$. The circuit forces the resistance of the thermo-resistive element alternately between $R_1 = 1/g_m G_1$ and $R_2 = 1/g_m G_2$. For a thermo-resistive element, the fixed resistances can only exist at corresponding fixed temperatures. Thus the servo loop provides the power to drive the thermo-resistive element between the two temperatures $T_1$, $T_2$ corresponding to the equilibrium resistances $R_1$ and $R_2$, respectively.

The power difference, $P_1 - P_2$, required to drive the temperature of the thermo-resistive element and the temperature levels $T_1$ and $T_2$ imply the dissipation coefficient, $\Delta P/\Delta T$, of the immersed thermo-resistive element, which is a function of the fluid velocity, as provided in Equation 1 (that is $\Delta P_{\Delta T} = A + BV^{\frac{1}{2}}$ where V is fluid velocity). When each equilibrium temperature $T_1$ or $T_2$ is reached, the current (28) through the thermo-resistive element is determined and the power is calculated using Joule's Law (i.e., $P = I^2R$). The change in applied power ($\Delta P = I_1^2 R_1 - I_2^2 R_2$) is divided by the calculated change in temperature ($\Delta T = T_1 - T_2$), to compute the dissipation coefficient, P/T for use in Equation 1.

Figure 4:
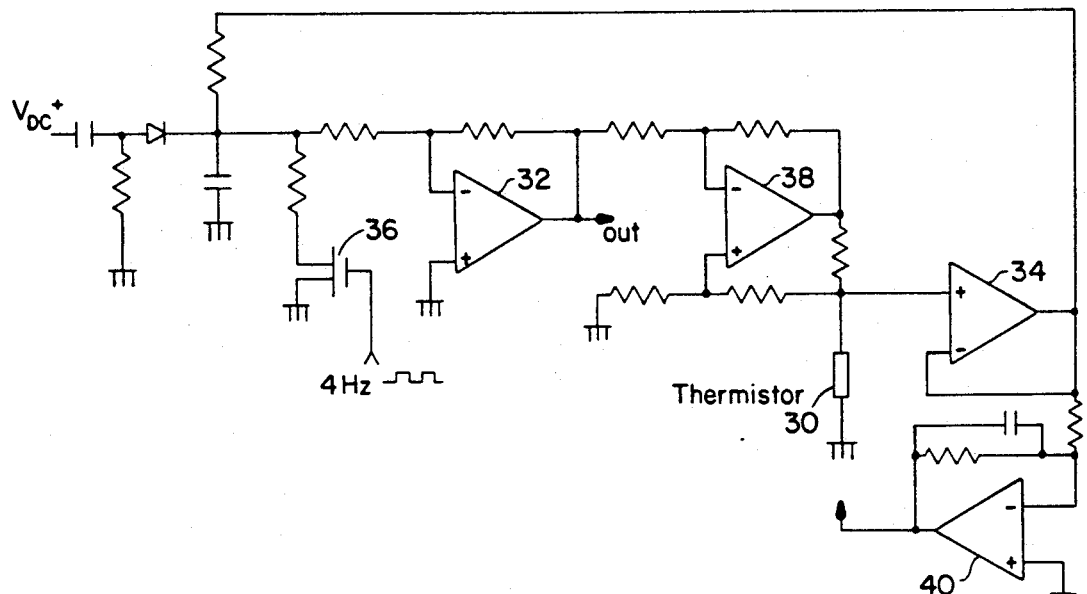
FIG. 4 is a detailed circuit schematic showing a specific implementation of the temperature servo embodiment of the present invention.

FIG. 4 shows a specific circuit implementation of the temperature servo embodiment. The thermistor 30 would be placed in a flow field. The variable gain amplifier employs amplifiers 34 and 32 and a FET switch 36. Amplifier 38 is wired as a voltage controlled current source and provides the transconductance function. Amplifier 40 can be used to provide an alternate thermistor return. If it is used, Equation 3 changes to $R = 1/2g_m G$. Use of the alternate thermistor return causes the net d.c. voltage of the thermistor to be zero at all times, which may reduce electrical cross-talk in some applications.

In the illustration given above, the amplifier produced a square wave having two states ($G_1$, $G_2$), which drove the thermo-resistive element along a resistance path having two equilibrium temperature states ($T_1$,$T_2$). When each equilibrium state was reached the current through the element 20 was determined. The power dissipated and the fluid velocity were calculated. It is to be understood that the output from the amplifier 24 or the transconductance circuit 26 can use other periodic waveforms. For instance, the temperature of the thermo-resistive element could be driven along a path having several step values. Alternatively, the temperature of the thermo-resistive element could be driven along a continuous path by having gain G(t) produced by amplifier 24 that varies according to a continuous periodic function, such as a sine wave function.

Continuously Controlled Gain Temperature Servo

Figure 5:
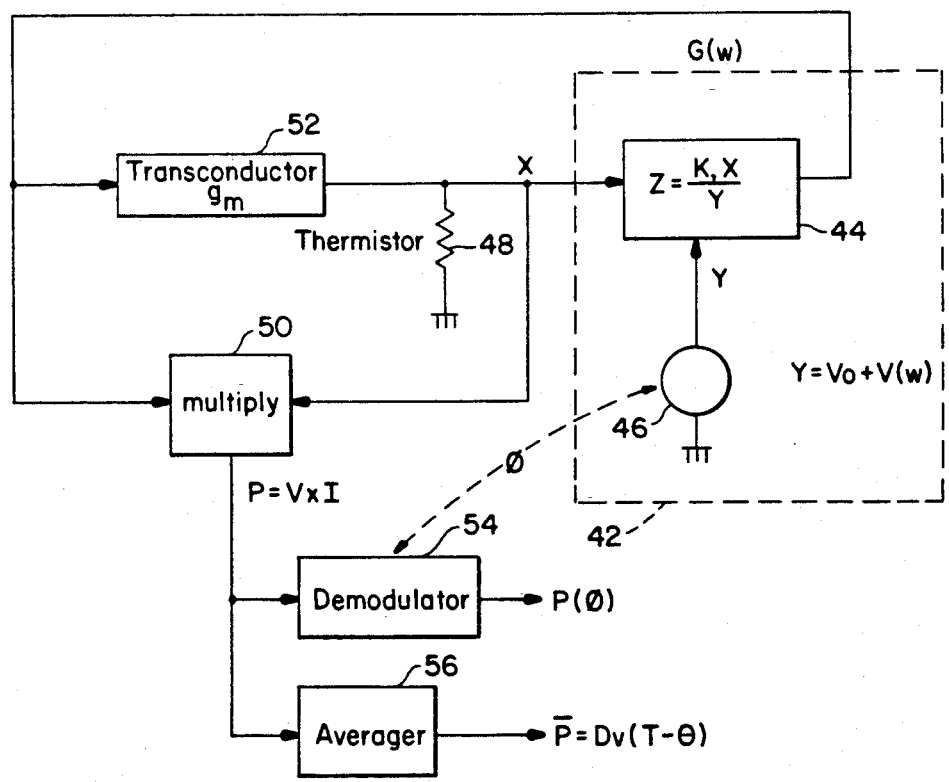
FIG. 5 is a schematic drawing of the temperature servo embodiment wherein a sinusoidal function is used to continually drive the thermo-resistive, element along a continuous periodic path.

Alternatively, the temperature of the thermo-resistive element can be driven along a temperature continuous path by controlling the gain (G) produced by the amplifier according to a continuous function, such as a sine wave function. FIG. 5 shows such an embodiment. The continually varying gain amplifier 42 consists of a divide circuit 44 and a voltage source 46. The voltage source produces a continuously varying voltage $Y = E_o + E(\omega)$. (If a sine wave function were used, the voltage supplied to the divide circuit would be $Y = E_{DC} + E \sin \omega t$.) The divide circuit 44 produces as an output the value $Z = K_1 yX$, where $K_1$ is an amplification constant, X is the input from the feedback loop and Y is the continuously varying voltage from source 46. The circuit equations imply that the resistance of the thermo-resistive element 48 is driven along the continuous path $$R = \frac{E_o + E(\omega)}{g_m K_1} \qquad \text{Equation 4}$$

where $V_o$ is a constant voltage and $V(\omega)$ is a zero mean time varying voltage. The resistance of certain thermo-resistive elements, such as thermo-resistors, varies nearly linearly with temperature for small changes in both quantities. Thus, thermo-resistive temperature variations can be forced to follow the voltage source variations $E(\omega)$ as closely as desired. This continuous functional control of the thermistor's temperature variation is useful in the operation of this embodiment. The power necessary to drive the thermistor along this temperature pathway is measured. Multiplier 50 receives as its input the voltage provided to the thermo-resistive element and a measure of the current driving the thermo-resistive element (as implied by the input to the transconductor 52). The output from multiplier 50 indicates the power required to drive the thermo-resistive element's resistance along the path defined by the above equation.

Utilizing an example where the voltage source 46 provides a sinuosidally varying voltage $E_o + E_s \sin \omega T$, the thermo-resistor is driven nearly along the following resistive path:

$$R = \frac{E_o + E_s \sin \omega T}{g_m K_1} \qquad \text{Equation 5}$$

The constant term $E_o/g_m K_1$ forces the thermistor to a mean temperature above the highest temperature expected in the fluid. The term $E_s \sin \omega t/g_m K_1$ forces resistance fluctuations in the thermo-resistor along a path $R_2 \cdot \sin \omega T$, and the temperature of the thermo-resistor is also driven along a nearly sinusoidal path. The power levels estimated by the multiplier, 50, are related to the power required to maintain the thermo-resistive element 48 at the various temperatures along the driven temperature path, and it is related to the rate of change of such temperatures. A phase sensitive demodulator 54 demodulates the power estimated by the multiplier 50 with a selected phase reference, $\phi$, relative tot h driving signal $E(\omega)$. In the case of simple sinusoidal drives, $\phi$ is selected to lock the demodulator to the phase of the given nearly sinusoidal temperature f the thermo-resistor 48 and the power variations, $\Delta P$, related to the temperature variations, $\leftarrow T$, (implied by the change in thermo-resistance $R_s$) are found, Then the flow-dependent dissipation rate $\Delta P/\Delta T$ is fond to solve for velocity in Equation 1. If the demodulator is phased so that the determined power is in quadature with the temperature fluctuations in the thermo-resistor, then a $\Delta P$ is found which is related to the heat capacity of the thermo-resistor and its surrounding fluid.

When the phase of the synchronous detector or demodulator is locked to the drive voltage $E(\omega)$, a double benefit is realized: (1) first, as fluid flow increases, the fluctuating power's magnitude increases; and (2) secondly, the phase of the power signal, P more nearly matches that of E(w) at the higher flow speeds, because the thermal time constant of the ventilated thermo-resistor-fluid system decreases with fluid speed. This pair of effects enhances the sensitivity of the so-determined $\Delta P/\Delta T$ ratio to fluid speed.

The fluid temperature can also be detected using the averaging circuit, 56. The relationship of average power to fluid temperature is given below:

$$P = (T - \theta)(\Delta P/\Delta T)$$

where
P is the mean thermistor power,
T is the mean thermistor temperature,
$\theta$ is the unknown fluid temperature. Knowing the fluid temperature ($\theta$) could be used to remove minor residual fluid temperature influences that couple into Equation 1 by way of viscosity, and thus increase the accuracy of the system. Similar techniques to determine fluid temperature are possible with the other embodiments shown.

The advantage of using a continuously-controlled gain temperature servo are three-fold. First, the output signal is sampled continuously, thus reducing unwanted effects resulting from fluid temperature fluctuations, turbulence effects, and circuit noise effects. Secondly, it may be implemented with purely analog components, eliminating the requirements for digital drive, sampling and voltage digitization. Thirdly, it can be implemented with any drive-function, $E(\omega)$ desired, including linear sinusoidal temperature control.

Power Servo Embodiment

Figure 6:
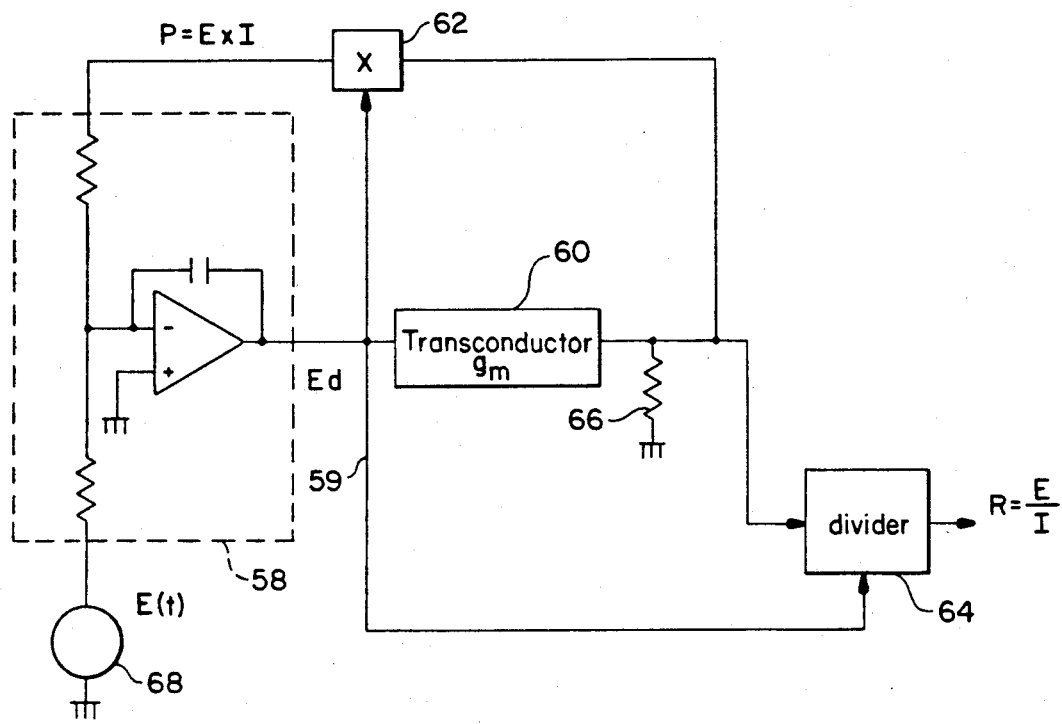
FIG. 6 is a schematic diagram showing an alternative embodiment where the thermo-resistive element is driven along a FIG. 7 is a schematic diagram of the present invention showing an alternative embodiment having a temperature sensing element and a separate resistive heater that are closely thermally coupled.

In the preceding embodiment of the invention, a temperature servo was used to drive the thermo-resistive element along the temperature path and the power necessary to drive the thermo-resistive element along that path was measured. In an alternative embodiment, a power-servo forces the drive power along a fixed path and measures, directly or indirectly, the resistance (and therefore temperature), of the thermo-resistive element. FIG. 6 shows a generic drawing of the power servo embodiment, which comprises a fast servo integrator 58, a transconductor 60, a multiplier 62, a divider 64, a thermo-resistive element 66, and a variable voltage driving source 68. The power to the thermo-resistive element is forced to be directly proportional to $E(t)$ generated by the voltage driving source 68. The servo circuit makes $E_d$ 59 take on whatever value that fores the power, calculated by the multiplier 62, to track the voltage drive source 68 $E(t)$. The resistance of the thermo-resistive element 66 is then computed from $R = E/I$, for example, appearing at the output of the divider 64. From the resistive values the temperatures of the thermo-resistive element are calculated. Again, T values are used to calculate the fluid velocity given by Equation 1

$$\left( \frac{\Delta P}{\Delta T} = A + Bt^{\frac{1}{2}} \right).$$

It is also possible to drive the thermo-resistor in a device like that in FIG. 6 directly from the servo integrator 58 and sense the current flowing through the thermo-resistor. That sensed current is again multiplied by the drive voltage to derive the applied power by a device such as 62 multiplier. In this case, the transconductor is absent. Again, power is determined by the product of the thermo-resistor's voltage and current, and resistance from the ratio.

Separate Heating and Sensing Elements

Figure 7:
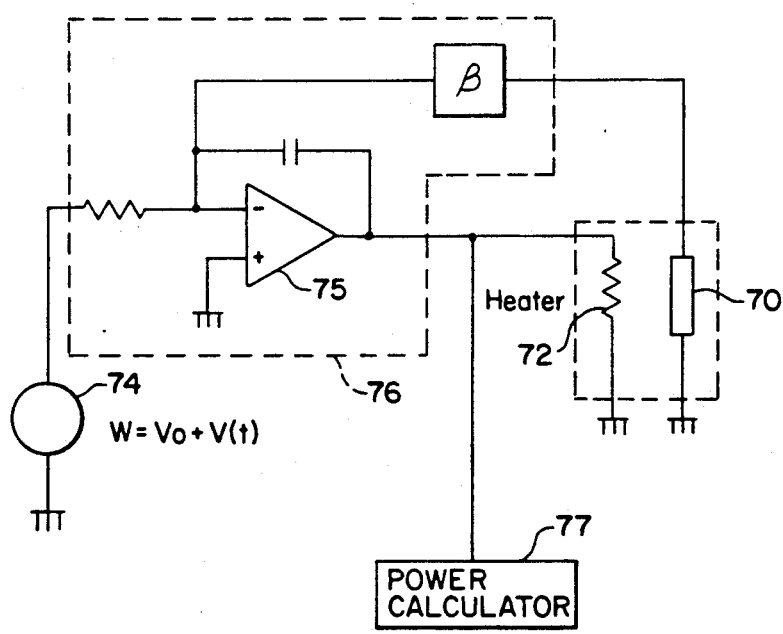

In the embodiments described thus far, the sensor is a self-heated thermo-resistive element. Such a restriction will be useful in many applications, but the invention extends to separate heating and sensing elements. FIG. 7 is a block diagram of one such embodiment. The temperature sensing element 70 is closely coupled with a resistive heater 72 of fixed or well characterized resistance. The sensor, 70, provides a current or voltage to provide a feedback signal scaled by some $\beta$ to the servo integrator, 76. The feedback circuit at the amplifier 75 forces the temperature output from heater 72 to track a waveform W generated by voltage source 74 ($W = E_o + E(t)$). The power required to cause the tracking is calculated using Joule's Law ($P = V \cdot I = V^2 R$ where V is the voltage and R is the resistance of the heater 72) by power calculator 77 which can be a digitizer and computer or analog multiplying circuits as is well known in the art This method can be used with a switched drive, in which the near-equilibrium states just prior to switching is used to find $\Delta T$ and $\Delta P$. It can also use continuous drive waveforms, particularly sinusoidals. When sinusoidal drive is supplied by voltage source 74, the component of power co-spectral with the driving temperature waveform, is closely related to the King's Law velocity component, and the quadspectral component is primarily related to the thermal inertia of the sensor.

What is claimed is:

1. An apparatus for measuring fluid flow comprising:
   a thermo-resistive element having a resistance that varies as a function of temperature and adapted to be exposed to fluid flow;
   a means for driving said thermo-resistive element along a controlled continuously varying temperature path; and,
   a means of measuring the power required to drive the thermo-resistive element along said temperature path, wherein the measured power is an indication of the rate at which heat is conducted away from e thermo-resistive element.

2. The apparatus of claim 1, wherein said driving means drives the thermo-resistive element along a periodic continuous temperature profile.

3. An apparatus for measuring fluid flow comprising:
   a thermal-resistive element having a negative temperature coefficient and adapted to be exposed to fluid flow;
   a means for driving said thermo-resistive element along a temperature path, wherein said drive means is a feedback loop for controlling resistance of said thermo-resistive element comprising:
   an amplifier providing gain, G, for amplifying the voltage that appears across the thermo-resistive element; and,
   a transconductor operably coupled to the output of said amplifier for providing a voltage controlled current source having a transconductance of $g_m$, where the output from the transconductor provides current to the thermo-resistive element; and
   a means for measuring the owe required to drive the thermo-resistive element along said temperature path, wherein the measured power is an indication to the rate at which heat is conducted away from the thermo-resistive element.

4. The apparatus of claim 3, wherein said amplifier provides at least two alternating gain values which force the resistance of the thermo-resistive element between at least two values.

5. The apparatus of claim 3, wherein said transconductor provides at least two alternating transconductance values which force the resistance of the thermo-resistive element between at least two values.

6. The apparatus of claim 3, wherein said amplifier provides a varying gain that allows a continuous periodic function which forces the resistance of the thermo-resistive element along a continuous path.

7. The apparatus of claim 3, wherein said transconductor provides a varying transconductance that follows a continuous periodic function which forces the resistance of the thermo-resistive resistive element along a continuous path.

8. The apparatus of claim 6, wherein said amplifier comprises:
a voltage source providing a continuous periodic varying voltage; and
a divider circuit receiving as inputs a value (x) of the voltage appearing across the thermo-resistive element and the output (y) from said voltage source, and providing an output (z) to the transconductor where $z \propto (x_y)$.

9. The apparatus of claim 6, wherein said means for measuring power continually measures the power dissipation as the resistance to the thermo-resistive element is force along said continuous path comprising:
a means for calculating the instantaneous power variations across the thermo-resistive element; and,
phase sensitive demodulator operably coupled to said calculating means and said voltage source for calculating power variations as a function of the phase relative to the periodic varying voltage supplied by said voltage source in said feedback loop.

10. The apparatus of claim 9, wherein said voltage source provides a sinusoidal drive voltage variation and the wherein the phase sensitive demodulator provides an output substantially in phase with the sinusoidal drive voltage variations, thereby relating changing power values to changing temperature values of the thermo-resistive element.

11. The apparatus of claim 9, wherein said voltage source provides a sinusoidal drive voltage variation and wherein the phase sensitive demodulator provides an output of a quadspectral component based on the phase of the sinusoidal drive voltage to provide information on thermal properties to the fluid.

12. An apparatus for measuring fluid flow comprising:
a thermo-resistive element having a resistance that varies as a function of temperature and adapted to be exposed to fluid flow;
a means for driving the power supplied to the thermo-resistive element along a continuously varying power path; and,
a means for measuring the resistance of the thermo-resistive element as it si driven along thepower path, wherein the measured resistance is an indication to the temperature of the thermo-resistive element and provides a measurement of fluid flow characteristics.

13. An apparatus for measuring fluid flow comprising:
a thermo-resistive element having a resistance that varies as a function of temperature and adapted to be exposed to fluid flow;
a means for driving thepower supplied to the thermo-resistive element along power path comprising a servo circuit, driven by a variable voltage source for providing power to the thermo-resistive element at a value that tracks the voltage levels provided by the variable voltage source, the servo circuit comprises:
a transconductor coupled to said thermo-resistive element, for providing a voltage controlled current drive to said thermo-resistive element;
a multiplier operably coupled to the thermo-resistive element for providing an output indicating the electrical power provided to the thermo-resistive element; and,
a servo integrator for making thepower provided to the thermo-resistive element track the voltage supplied by the variable voltage source by supplying the appropriate control voltage to the transconductor; and
a means for measuring the resistance of the thermo-resistive element as it is driven along thepower path, wherein the measured resistance is an indication of the temperature of the thermo-resistive element and provides a measurement of fluid flow characteristics.

14. An apparatus for measuring fluid flow comprising:
a thermo-resistive element having a resistance that varies as a function of temperature and adapted to be exposed to fluid flow;
a means for driving thepower supplied to the thermo-resistive element along a power path comprising a servo circuit driven by a variable voltage source for providing power to the thermo-resistive element at a value that tracks the voltage levels supplied toby the variable voltage source, the servo circuit comprises:
means connected to said thermo-resistive element to measure the current flowing therein;
a multiplier operably coupled to the thermo-resistive element and responsive to the current flowing therein and the voltage supplied thereto for providing an output indicating the electrical power provided to the thermo-resistive element; and,
a servo integrator for making the power provided to the thermo-resistive element track the voltage supplied by the variable voltage source by supplying the appropriate control voltage to the transconductor; and
a means for measuring the resistance of the thermo-resistive element as it is driven along the power path, wherein the measured resistance is an indication of the temperature of the thermo-resistive element and provides a measurement of fluid flow characteristics.

15. An apparatus for measuring fluid flow comprising:
a temperature sensing element closely coupled with a resistance heater;
a means connected by a feedback loop to the temperature sensing element for forcing the temperature output from the resistive heater to track a preselected temperature path; and,
a means for measuring the power required to drive the resistive heater along said preselected temperature path, wherein the measured power is an indication of the rate at which heat is conducted away from the resistive heater.

16. The apparatus of claim 15, wherein said preselected temperature path contains at least two equilibrium temperature states.

17. The apparatus of claim 15, wherein said preselected temperature path is a continuous periodic waveform.

18. The apparatus of claim 17, wherein the periodic waveform is a sinusoidal and wherein said measuring means measures the power component co-spectral with said sinusoidal as an indication of fluid velocity.

19. The apparatus of claim 17, wherein the periodic waveform is a sinusoidal and wherein said measurement means measures the quadspectral power component to said sinusoidal to measure thermal inertia of the temperature sensor.

* * * * *